United States Patent
Schürenkrämer et al.

(10) Patent No.: US 6,647,595 B2
(45) Date of Patent: Nov. 18, 2003

(54) DEVICE ON A CLEANER, A CARDING MACHINE OR THE LIKE FOR CLEANING AND OPENING TEXTILE MATERIAL

(75) Inventors: Michael Schürenkrämer, Mönchengladbach (DE); Thomas Steinert, Kerpen (DE)

(73) Assignee: Trützschler GmbH & Co. KG, Mönchengladbach (DE)

( * ) Notice: Subject to any disclaimer, the term of this patent is extended or adjusted under 35 U.S.C. 154(b) by 0 days.

(21) Appl. No.: 10/189,143

(22) Filed: Jul. 5, 2002

(65) Prior Publication Data

US 2003/0005551 A1 Jan. 9, 2003

(30) Foreign Application Priority Data

Jul. 5, 2001 (DE) .......................... 101 32 711

(51) Int. Cl.[7] .............................................. D01G 15/46
(52) U.S. Cl. ...................................... 19/106 R; 19/105
(58) Field of Search ........................ 19/106 R, 65 R, 19/65 A, 200, 203, 204, 205, 105, 107, 108, 109; 209/577, 587; 250/222.2, 223 R; 356/238.1, 238.2, 238.3, 429, 430

(56) References Cited

U.S. PATENT DOCUMENTS

| 4,262,806 A | * | 4/1981 | Drabs ......................... 209/577 |
| 4,657,144 A | * | 4/1987 | Martin et al. ............... 209/546 |
| 4,909,930 A | | 3/1990 | Cole |
| 5,084,942 A | | 2/1992 | Schelb et al. |
| 5,107,571 A | | 4/1992 | Marzoli et al. |
| 5,544,090 A | * | 8/1996 | Shofner et al. ............... 702/82 |
| 5,692,267 A | | 12/1997 | Leifeld |
| 6,029,317 A | * | 2/2000 | Meile et al. ............... 19/145.5 |

FOREIGN PATENT DOCUMENTS

| DE | 26 13 921 A1 | 10/1976 |
| DE | 43 40 173 A1 | 6/1995 |
| DE | 196 04 499 A1 | 10/1996 |
| DE | 196 43 406 A1 | 4/1998 |
| DE | 39 28 279 C2 | 5/1998 |
| DE | 199 55 292 A1 | 5/2001 |
| EP | 0 967 305 A1 | 12/1999 |
| GB | 265 130 | 8/1927 |
| GB | 2 200 147 A | 7/1988 |
| GB | 2 340 137 A | 2/2000 |
| WO | WO 90/11392 | 10/1990 |

* cited by examiner

*Primary Examiner*—Gary L. Welch
(74) *Attorney, Agent, or Firm*—Venable LLP; Robert Kinberg; Stuart I. Smith

(57) ABSTRACT

In order to detect and remove interfering particles, particularly trash particles, husk naps, seed remnants and the like, from textile fiber goods, a device on a carding machine, a cleaner or the like is provided across the width of the carding machine, cleaner or the like with at least one detection device, for example, a camera with an electronic evaluation device for the detection, and a downstream-connected separating device for removing the particles. A plurality of guide elements are provided across the width, which can selectively deflect the fiber goods regions containing the interfering particles to improve the effect of the separating device in a simple manner.

28 Claims, 3 Drawing Sheets

DEVICE ON A CLEANER, A CARDING MACHINE OR THE LIKE FOR CLEANING AND OPENING TEXTILE MATERIAL

CROSS-REFERENCE TO RELATED APPLICATION

This application is based on and claims the priority date of German Application No. 101 32 711.0, filed on Jul. 5, 2001, which is incorporated herein by reference in its entirety.

FIELD OF THE INVENTION

The invention relates to a device on a carding machine, a cleaner or the like for detecting and removing foreign particles, in particular, trash particles, husk naps, seed remnants and the like from textile fiber goods.

BACKGROUND OF THE INVENTION

Separation knives for removing waste material, trash and dust are used on carding machines and cleaners. On cleaners, these knives are used in connection with saw-tooth rollers, while on carding machines they are used in particular with licker-ins. However, they can also be assigned to pin rollers. The knives are frequently used in combination with suction hoods or suction pipes. The suction hoods in that case must transport off the trash, short-fiber particles and dust particles in the airflow. The knives are adjusted in a stationary fashion, meaning the knife location, the distance between knife tip and roller and the angular position of the knife-separation flank relative to the roller tangent are constant during the machine operation. The disadvantage is that changing the individual adjustment parameters is frequently difficult and can therefore be effected only if the machine is stopped. The distance between knife edge (tip) and the saw-tooth clothing on the licker-in can be between 0.2 and 0.6 mm, depending on the fiber material to be processed. The adjustment must be made manually, while the machine is stopped, using a so-called distance gauge. The knife, for example, is adjusted to adapt it to different types of materials, in particular to different types of dirt or the dirt content. In practical operations, the separating knife is designed as a one-piece, continuous knife blade that extends over the width of the machine. One disadvantage of the known separating knives is that an adaptation to locally different contents or local concentrations or the adaptation of individual elements to foreign bodies in the fiber material, such as waste, naps, seed fragments, trash particles and the like, is not possible.

SUMMARY OF THE INVENTION

An object of the invention therefore is to create a device of the aforementioned type that avoids the previously mentioned disadvantages and, in particular, provides an easy way to improve the effectiveness of the separating device.

This object is solved with a device comprising at least one detecting device that extends across the width of the machine, for example, a camera with electronic evaluation device, and, in a downstream direction, means for selectively deflecting portions of textile fiber material flowing through the machine and for removing unwanted particles. The means for selectively deflecting and for removing comprises a plurality of parallel elements that are able to be individually activated for selective removal of the unwanted particles. In particular, such a device on a carding machine, a cleaner or the like for detecting and removing troublesome particles, in particular, trash particles, husk naps, seed remnants, and the like, from textile fiber goods, comprises at least one detection device across the width of the machine, for example, a camera with electronic evaluation device for the detection, and in a downstream direction, a separating device for removing the particles. The separating device is characterized in that a multitude of guide elements are present across the width covered by the detection device, and the separating device can selectively deflect the regions of the fiber material with the interfering particles. By so doing, the separating device permits selective separation by one or more separation knives.

An individual adaptation or an increase in the separation of individual foreign bodies or local concentrations of several foreign bodies is easily possible because the many guide elements provided can selectively deflect the fiber material. The effectiveness of the separating device is improved considerably in this way, wherein the separating out is focused only on the individual particles and is thus strengthened. An additional advantage is that the separating device does not affect the fiber material regions that do not contain foreign bodies.

The invention may include various additional features. These include, for example:

- movable guide elements, which may be actuated individually under control of the detection device, as to both time of deflection and which element or elements are deflected;
- guide elements having individual controllable adjustment devices, which may have inductive, pneumatic, and/or piezoelectric elements;
- an optical detection device, like a camera, which may be connected to an electronic image-processing device, which may further include a control device (like a computer); and
- a joint suction device may be used across the device to remove the foreign bodies.

The invention comprises an additional, advantageous device on a cleaner, a carding machine or the like for cleaning and opening textile fiber material, particularly cotton, with a rotating clothing or pin roller that is installed downstream of the feeding device. The roller is enclosed by a housing having at least one opening for removing impurities such as trash particles, leaf remnants, seed husks, stem remnants, sand and the like, wherein at least one separating knife is assigned to the clothing or pins of the clothing or pin roller. A knife blade facing in the direction counter to the rotational direction for the clothing or pin roller is arranged at the opening. The separating knife consists of a plurality of knife elements, and the distance between the individual knife elements and the clothing or pins for the clothing or pin roller can be changed.

The separation can easily be changed or adapted individually to locally different contents or local concentrations, if necessary, up to the size of the individual foreign body, since the separating knife consists of a plurality of knife elements, for which the distance to the roller can be adjusted or changed individually. A defined separation takes place. In the process, a selective short-term separation (a foreign body is detected and separated out individually), as well as a long-term differentiated adjustment of the individual knife elements, is possible across the width of the machine, e.g., for counteracting detected accumulations of foreign bodies across the width of the machine.

In another embodiment, the invention comprises a device on a cleaner, a carding machine or the like for cleaning and opening textile fiber material, said device comprising a rotating clothing or pin roller that is installed downstream of a feeding device, and which is surrounded by a housing with at least one opening for removing impurities such as trash particles, leaf remnants, seed husks, stem fragments, sand and the like. The invention further comprises at least one separating knife that is assigned to the clothing or the pins of the clothing or pin roller, which separating knife has a knife edge pointing in a direction counter to a rotational direction of the clothing or/pin roller, and which is arranged at the at least one opening. This is characterized in that the separating knife consists of a plurality of knife elements and that the distance between the individual knife elements and the clothing or the pins of the clothing or pin roller can be changed. Further modifications to the invention are also possible, including, for example:

- the spacings between the knife elements and the clothing or the pins of the clothing or pin roller may be adjusted permanently or adaptively (temporarily) and may be adjusted in dependence upon factors like the amount, accumulation, etc., of impurities;
- the timing of selection of/spacing changes between knife elements may be under the control of the detection device;
- the knife elements may comprise an elastic material (e.g., steel);
- an adjustment device for the knife elements may comprise electromagnetic elements;
- a joint suction device may be provided to the knife elements, to remove the impurities; and
- guide elements may be installed upstream of the separating knife.

BRIEF DESCRIPTIONS OF THE DRAWINGS

The invention is explained in further detail in the following with the aid of drawings showing exemplary embodiments, in which FIG. 1 shows a schematic view from the side of a carding machine with a support and guide element for the fiber web and showing three locations for installing the device according to the invention;

DETAILED DESCRIPTION OF EMBODIMENTS OF THE INVENTION

Figure 1:
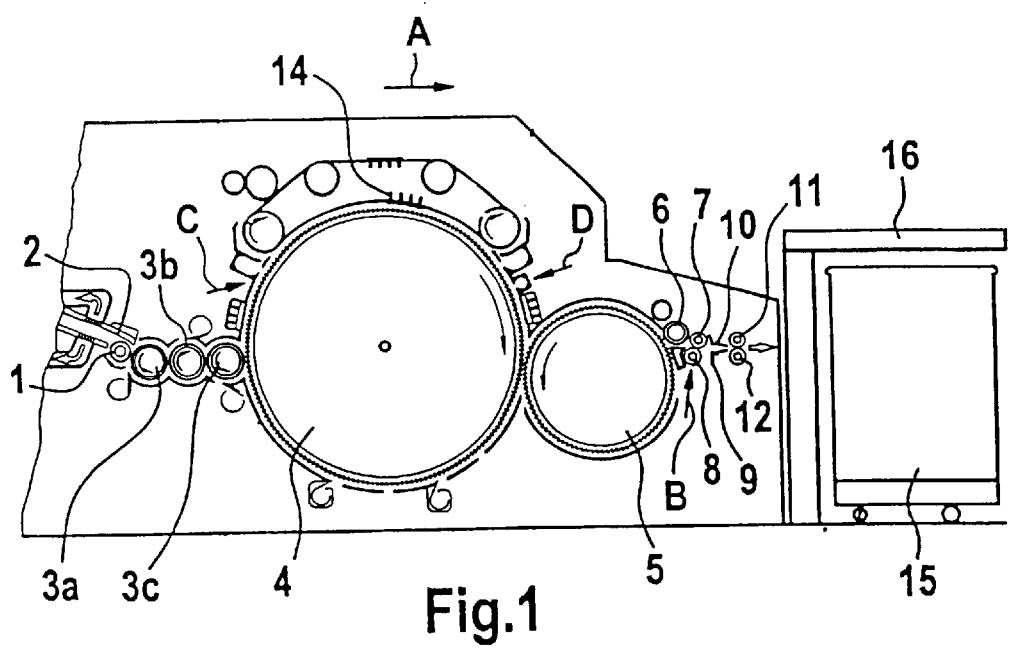
Figure 2:
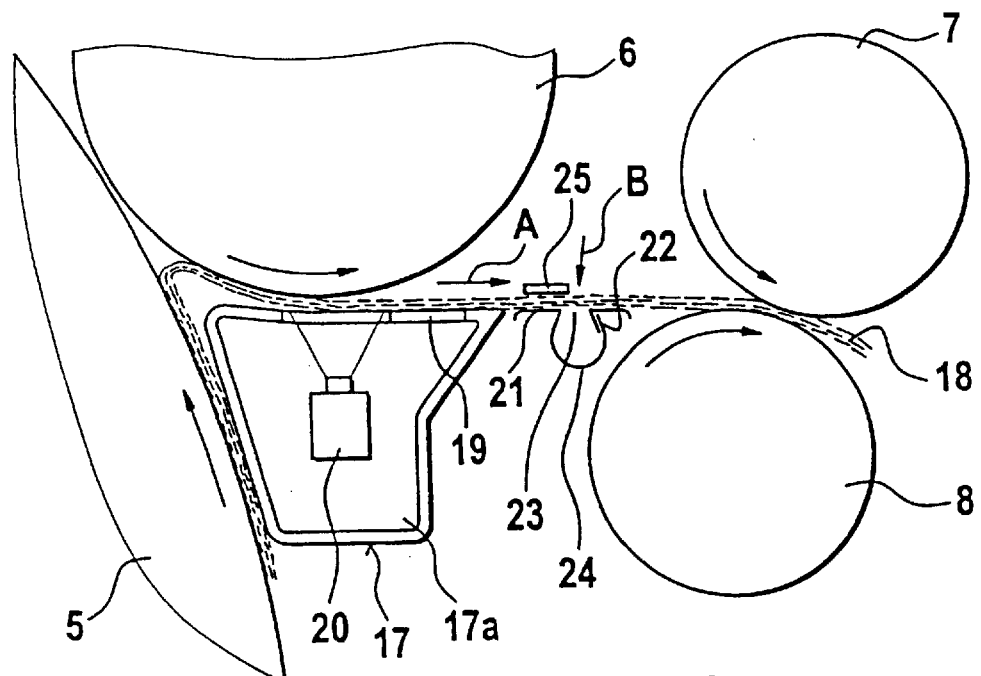
FIG. 2 shows a view from the side of a first embodiment of the device according to the invention, installed between the stripping roller and the crushing rollers of a carding machine.

FIG. 1 shows a carding machine, for example, a Trützschler high-performance carding machine DK 903, comprising feed roller 1, feed table 2, licker-ins 3a, 3b, 3c, main carding cylinder 4, doffer 5, stripping roller 6, crushing rollers 7, 8, sliver guide element 9, web trumpet 10, withdrawing rollers 11, 12, traveling flats 14, can 15 and sliver coiler can arrangement 16. Curved arrows indicate the rotational direction of the rollers. The letter A indicates the operating direction. A support and guide element 17 for the web 18 is arranged below the stripping roller 6, as shown in FIG. 2. The letter B refers to the area where the web is lifted off and transferred from the support and guide element 17 to the roller gap between the crushing rollers 7, 8. A first embodiment of the invention is arranged in the region B (see FIGS. 2 to 4). Another embodiment of the invention is arranged in the regions C and D, which are assigned to the main carding cylinder 4 (see FIG. 6).

The support and guide element 17 shown in FIG. 2 essentially has a rectangular cross section, wherein the upper surface has a slightly concave curvature. The curvature radius of the surface is larger than the curvature radius of the stripping roller 6. The arrow A indicates the direction in which the web 18 moves. The front-end region is provided with an edge while the back-end region is rounded. The edge prevents the deposit of impurities such as honeydew. The web 18 gliding across the contact/gliding region of the surface cleans this surface, for example, of trash. The cross-sectional shape of the element 17 is adapted to the airflow conditions in the region between doffer 5, stripping roller 6 and crushing rollers 7, 8. The element 17 serves as support and guiding element for the web 18. The element 17 is designed as a housing, wherein a translucent window 19 is provided in the contact region. The web is initially located on the clothing of doffer 5 and is deflected and transferred in the roller gap between doffer 5 and stripping roller 6 to the clothing of stripping roller 6. From the stripping roller 6, it is separated somewhat in a perpendicular direction and is guided in the contact/gliding region on the surface in the direction A. Subsequently, it moves through the region B toward the end region. Finally, it enters and moves through the roller gap between the crushing rollers. A camera 20, e.g., a diode line-scanning camera, and a lighting device that may consist of several light-emitting diodes, are arranged on the inside 17a of housing 17. A first embodiment of the device according to the invention is arranged in the region B, between the elements 17 and the roller gap between crushing rollers 7, 8. The fiber material 18 moves across a support element 21, which is followed by a separating knife 22 with separation opening 23 and suction hood 24. A guide member 25, consisting of a plurality of guide elements 25a to 25n (see FIG. 3), is present above the fiber material 18. Without being activated, these just barely glide over the fiber material 18 or do not even make contact with the material.

Figure 3:
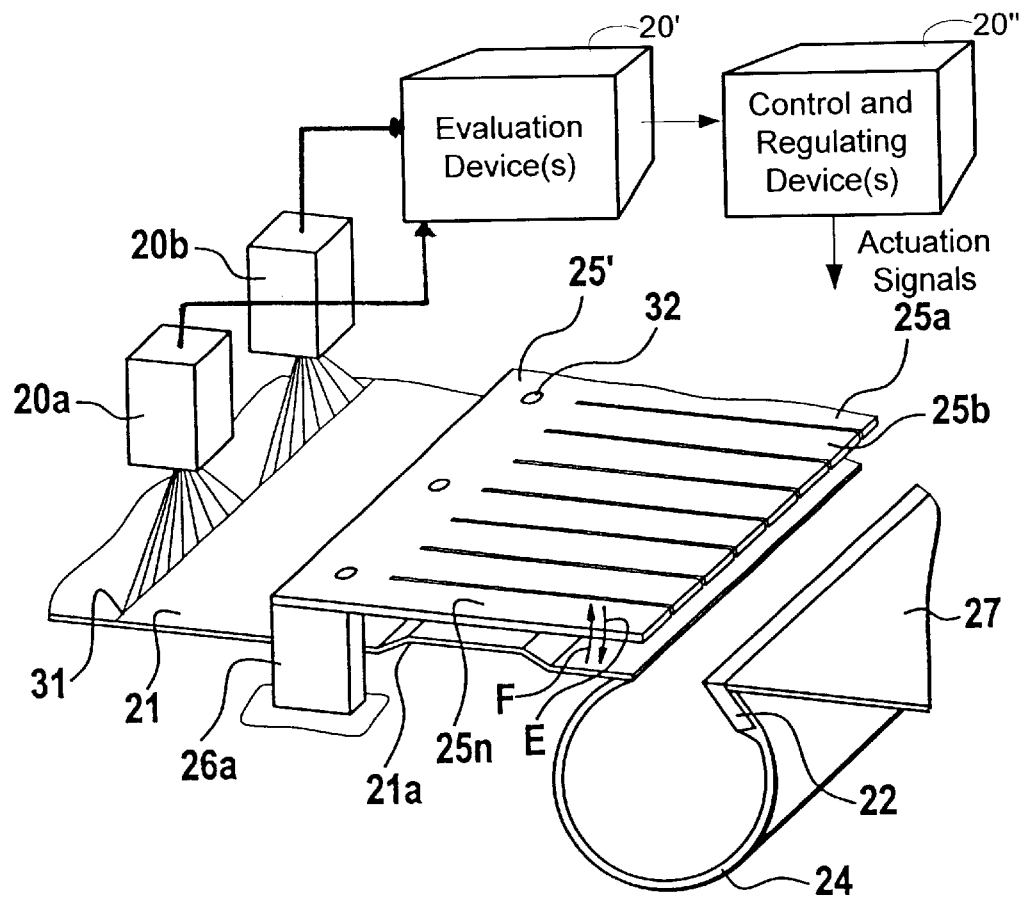
FIG. 3 shows a perspective representation of the device according to the invention, provided with two cameras.

FIG. 3 shows the support element 21, comprising two cameras 20a, 20b arranged across its width, which are connected to at least one image evaluation device 20'. At least one electronic control and regulating device 20" is further provided to produce actuation signals (e.g., electrical pulses) that control the guide elements 25a to 25n, based on the output of image evaluation device 20'. These devices can be designed, for example, in accordance with German Patent Application 196 04 499.5 (and in U.S. Pat. No. 5,692,267, assigned to the assignee of this application, and incorporated herein by reference in its entirety). Alternatively, electronic control and regulating device 20" may be incorporated into image evaluation device 20'. The support element 21, for example, a sheet metal piece, has a convex area 21a underneath the guide element 25a to 25n, which forms a narrowed section. An additional sheet-metal guide 27 is arranged downstream of the separating knife 22. The guide element 25 is designed to resemble a comb with the one end of guide elements 25a to 25n attached to a joint sheet-metal holder 25' while the other end of guide elements 25a to 25n is respectively open. The holder 25' is rigidly attached to two supports 26a, 26b (only 26a is shown herein), for example, with screws 32. The guide elements 25a to 25n are elastic and are deflected in the direction of arrows B or F, respectively, for activation and deactivation.

Figure 4:
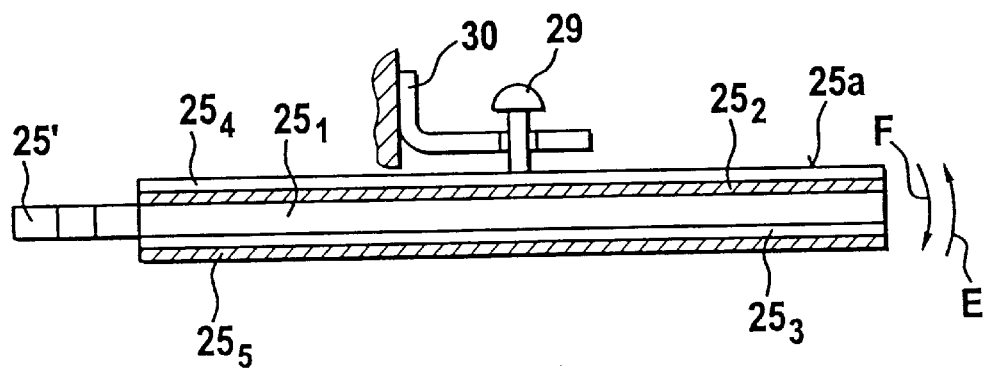
FIG. 4 shows a sectional cut through a guide element with a piezoelectric transducer.

The guide element 25a, attached to the holder 25', is designed according to FIG. 4 as a piezoceramic transducer. A central carrier material $25_1$ exists, on which is provided on each of both upper and lower surfaces, respectively, a piezoceramic layer $25_2$, $25_3$. A contacting and protective layer $25_4$, $25_5$ is deposited on the outside over each of the piezoceramic layers $25_2$, $25_3$. A mechanical path limiter is given the reference 29, 30.

Figure 5:
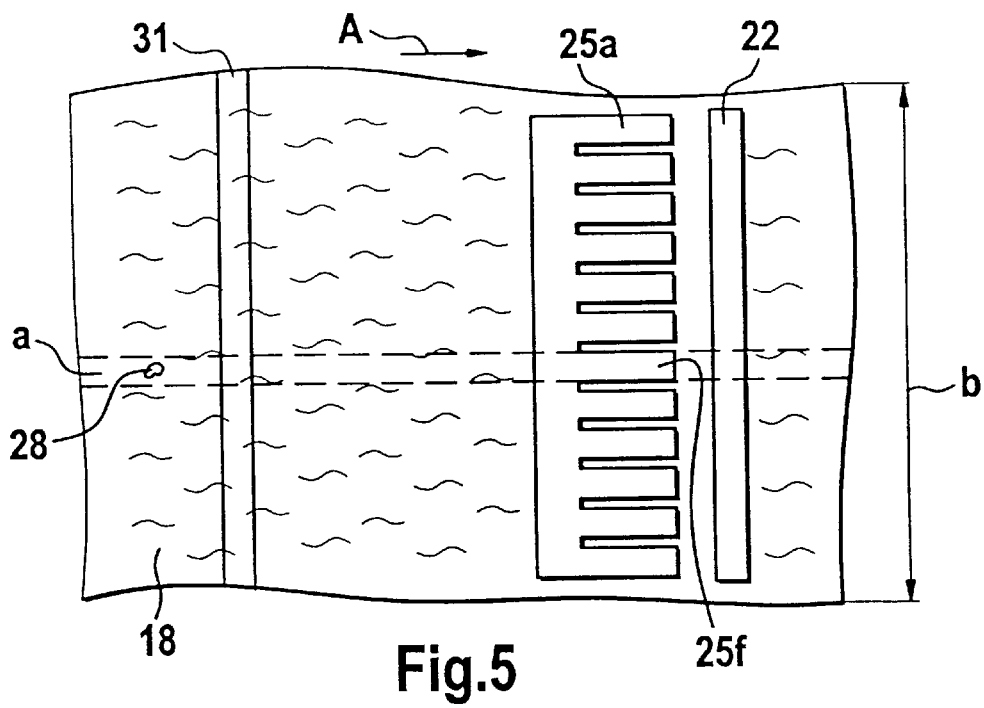
FIG. 5 shows a view from above of the fiber material with a foreign body, the detection range, the guide elements and the separating knife.

FIG. 5 schematically shows that a foreign body 28 located in the region a of the fiber material 18—which moves below the cameras 20a, 20b in the direction A—is recorded (detected) during the operation. An electrical pulse is then generated via the control and regulating device, through which the guide element 25f in region a is deflected downward in the direction of arrow E (FIG. 3) as a result of the piezoelectric effect. The guide element 25f only, therefore, pushes the fiber-material region a with foreign body 28 downward, so that the distance to the knife edge of the separating knife 22 is reduced, meaning the separating out of the foreign body 28 is made easier. The selective separating out of foreign bodies 28 is improved in this way. The detection region of cameras 20a, 20b is given the reference 31 in FIG. 5.

Cleaning machines, carding machines and combing machines in fiber-preparation systems, among other things, are designed to remove foreign bodies from the processed material. In the case of cotton, these are naps, seed fragments (even husk naps) and different size trash particles. The separation is based on the physical differences between these foreign bodies and the fiber material. As a rule, these differences involve density, mass-surface ratio (coefficient of fineness, flow resistance) and differences in the connection to the fiber web. By using these differences, the material is subjected to accelerations and/or flows of air, which are measured and oriented such that, preferably, the foreign bodies are separated out. The process of separating out, therefore, is not specifying, and the complete material flow is subjected to it. As a result of the above-mentioned physical differences, the statistical mean shows an accumulation of foreign bodies in the waste material.

Essential to the invention is a combination unit consisting of a detection unit (cameras 20a, 20b) with hardware and software that scans the complete machine width and generates actuating signals from the detection result for an actuator-moved guide element, a guide element 25 that can be individually triggered over the machine width and moved with an actuator, and a continuously operating separating element (knife 22). At the height of the detection line 31, the complete fiber mass flow 18 that flows past is scanned and is examined for foreign bodies 28. Besides the image processing method (several cameras and evaluation units that may, for example, be the same as those in the Trützschler NCT), other methods can also be used for this. Based on a predetermined threshold, an evaluation logic is used to decide which of the detected foreign bodies 28 are to be separated out. In addition to the desire to have the lowest amount of foreign bodies 28 in the end product, it must be taken into account that each time material is separated out, it represents a reduction in the previously scanned fiber amount and thus impairs the later band uniformity (CV value). The detection device 20 is followed by the guide element 25, which deflects the fiber mass flow 18 from the predetermined movement direction in a very small region of the machine width or the fiber-material width b. This arrangement is based on the idea of dividing the individual handling of the foreign body 28 and the actual separating-out operation. It is important that the fiber web 18 is partially deflected on the basis of the previously described detection and at the correct location to the effective range of a continuously operating separating device 22. The forces required for this are low, so that piezoceramic transducers, for example, can be used advantageously. Other fast-switching actuators, e.g., electromagnetic transducers, pneumatic cylinders and the like, can also be used. The arrangement is completed with the separation line, which can be either a suction hood 24 with separating knife 22 or a fast-rotating separating roller.

Figure 6:
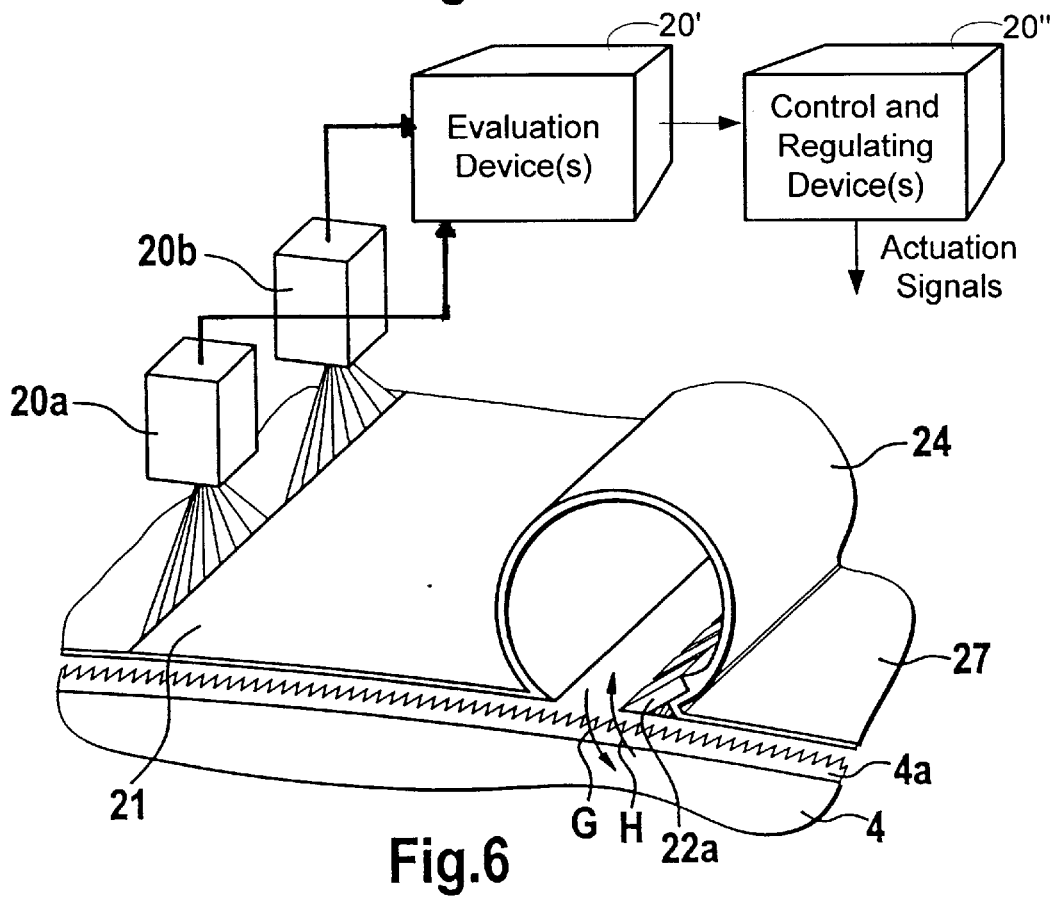
FIG. 6 shows a different embodiment with segmented separating knives that can be deflected individually.

The separating knife 22 of another embodiment according to FIG. 6 comprises a plurality of knife elements 22a to 22n across the machine width (in FIG. 6, only knife element 22a is shown in its entirety and labeled). The knife elements can be actuated individually and can be deflected in the direction of arrows G, H. As compared to the embodiment according to FIGS. 2 to 5, the (segmented) separating knife of the suction hood in this case replaces the (segmented) guide element 25. For the separating out of a foreign body 28 from the fiber material, the knife element, for example 22c, is allowed to locally approach the clothing 4a of the rotating main carding cylinder 4 in the direction G.

In addition to adjusting the selective short-term separation (a foreign body 28 is detected and individually selected), the individual knife segments can also be adjusted differently with the aid of the LGW (inside distance between front and back plate) and on the basis of the scanning described above (e.g., using the system as in the Trützschler NCT). This adjustment is designed to counteract, for example, via LGW, the detected accumulation of foreign bodies 28.

The invention has been described in detail with respect to preferred embodiments, and it will now be apparent from the foregoing to those skilled in the art that changes and modifications may be made without departing from the invention in its broader aspects. The invention, therefore, as defined in the appended claims, is intended to cover all such changes and modifications as fall within the true spirit of the invention.

What is claimed is:

1. A device for detecting and removing unwanted particles from textile fiber goods flowing through a machine for processing the textile fiber goods, the device comprising:
   at least one detection device for being disposed across a width of the machine and for detecting the unwanted particles; and
   means for selectively deflecting portions of the textile fiber goods flowing through the machine and for removing the unwanted particles, the means for selectively deflecting and for removing for being disposed downstream of the at least one detection device, relative to the flow of the textile fiber goods through the machine,
   wherein the means for selectively deflecting and for removing comprises
      a plurality of parallel guide elements that are able to be individually activated for selective removal of the unwanted particles;
      a separating device; and
      a guide apparatus for being disposed across the width of the machine between the at least one detection device and the separating device.

2. The device according to claim 1, wherein the guide apparatus comprises:

the plurality of guide elements for being disposed across the width of the machine between the at least one detection device and the separating device, said guide elements being arranged for selectively deflecting portions of fiber material flowing through the machine that contain the unwanted particles detected by the at least one detection device.

3. The device according to claim 2, wherein said at least one detection device comprises:
at least optical detection device; and
at least one electronic evaluation device coupled to the at least one optical detection device for evaluating an output of the at least one optical detection device.

4. The device according to claim 3, wherein the at least one electronic evaluation device comprises an electronic image-processing device.

5. The device according to claim 3, further comprising:
at least one control and regulating device receiving an output of the at least one electronic evaluation device and producing actuation signals based on the output of the at least one electronic evaluation device.

6. The device according to claim 3, wherein the guide elements are movable, and wherein the at least one evaluation device includes at least one control and regulating device and produces actuation signals for actuating movement of at least one of the movable guide elements.

7. The device according to claim 2, wherein each of said guide elements comprises a piezoelectric device.

8. The device according to claim 2, wherein each of said guide elements is controlled using at least one inductive element.

9. The device according to claim 2, wherein each of said guide elements is controlled using at least one pneumatic element.

10. The device according to claim 2, wherein said deflecting occurs essentially in a direction perpendicular to an operating direction of the machine.

11. The device according to claim 2, further comprising a counter surface, wherein the fiber material flows between the guide elements and the counter surface.

12. The device according to claim 2, further comprising:
a guide body provided with a joint holding area, wherein said guide elements are attached to the guide body and are open on one side.

13. The device according to claim 1, wherein the separating device comprises:
a separating knife.

14. The device according to claim 1, further comprising:
a joint suction device, associated with the means for selectively deflecting and for removing, for removing the unwanted particles.

15. The device according to claim 1, wherein the at least one detection device controls a time of deflection of at least one of the plurality of parallel elements.

16. A device for detecting and removing unwanted particles from textile fiber goods flowing through a machine for processing the textile fiber goods, the device comprising:
at least one detection device for being disposed across a width of the machine and for detecting the unwanted particles; and
means for selectively deflecting portions of the textile fiber goods flowing through the machine and for removing the unwanted particles, the means for selectively deflecting and for removing for being disposed downstream of the at least one detection device, relative to the flow of the textile fiber goods through the machine, wherein the means for selectively deflecting and for removing comprises a plurality of parallel knife elements that are able to be individually activated for selective removal of the unwanted particles, and the machine includes at least one of a rotating clothing and a pin roller installed downstream of a feeding device feeding fiber material, the at least one of a rotating clothing and a pin roller being surrounded by a housing with at least one opening for removing said unwanted particles, and wherein the means for selectively deflecting and removing comprises:
at least one separating knife associated with the clothing or the pins, respectively, of the clothing or pin roller, the separating knife comprising:
the plurality of knife elements, wherein a distance between each of the individual knife elements and the clothing or the pins of the clothing or pin roller is changeable, the plurality of knife elements forming a knife edge pointing in a direction counter to a rotational direction of the clothing or pin roller and arranged at the opening.

17. The device according to claim 16, wherein said at least one detection device comprises:
at least optical detection device; and
at least one electronic evaluation device coupled to the at least one optical detection device for evaluating an output of the at least one optical detection device.

18. The device according to claim 16, wherein the at least one electronic evaluation device comprises an electronic image-processing device.

19. The device according to claim 16, further comprising:
at least one control and regulating device receiving an output of the at least one electronic evaluation device and producing actuation signals based on the output of the at least one electronic evaluation device.

20. The device according to claim 16, wherein the knife elements are movable, and wherein the at least one evaluation device includes at least one control and regulating device and produces actuation signals for actuating movement of at least one of the movable knife elements.

21. The device according to claim 16, wherein said distance between each of the knife elements and the clothing or the pins of the clothing or pin roller is adjusted in dependence on characteristics of impurities in the fiber material.

22. The device according to claim 21, wherein at least one of said characteristics is detected using said at least one detection device.

23. The device according to claim 16, further comprising a joint holder to which each of said knife elements is individually attached.

24. The device according to claim 16, wherein each of the knife elements comprises an elastic material.

25. The device according to claim 16, wherein said separating knife further comprises:
a plurality of adjusting elements, each respectively associated with one of the knife elements.

26. The device according to claim 25, wherein at least one of said adjusting elements comprises an electromagnetic element.

27. A device for detecting and removing unwanted particles from textile fiber goods flowing through a machine for processing the textile fiber goods, the device comprising:
at least one detection device for being disposed across a width of the machine and for detecting the unwanted particles;

a separating device for removing the unwanted particles, the separating device for being disposed downstream of the at least one detection device, relative to the flow of the textile fiber goods through the machine; and a plurality of guide elements for being disposed across the width of the machine between the at least one detection device and the separating device, said guide elements being arranged for selectively deflecting portions of fiber material flowing through the machine that contain the unwanted particles detected by the at least one detection device.

28. A device for detecting and removing unwanted particles from textile fiber goods, the device for being disposed on a machine for processing such textile fiber goods, the machine including at least one of a rotating clothing and a pin roller installed downstream of a feeding device feeding fiber material, the at least one of a rotating clothing and a pin roller being surrounded by a housing with at least one opening for removing said unwanted particles the device comprising:

at least one detection device for being disposed across the width of the machine; and at least one separating knife associated with the clothing or the pins, respectively, of the clothing or pin roller, the separating knife comprising:

a knife edge pointing in a direction counter to a rotational direction of the clothing or pin roller and arranged at the opening; and a plurality of knife elements, wherein a distance between each of the individual knife elements and the clothing or the pins of the clothing or pin roller is changeable.

* * * * *